(12) United States Patent
Liu

(10) Patent No.: US 11,950,926 B2
(45) Date of Patent: Apr. 9, 2024

(54) ELECTRONIC DEVICE WITH MAGNETIC ASSEMBLY

(71) Applicant: Advanced Semiconductor Engineering, Inc., Kaohsiung (TW)

(72) Inventor: Chao Wei Liu, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 84 days.

(21) Appl. No.: 17/705,213

(22) Filed: Mar. 25, 2022

(65) Prior Publication Data

US 2023/0301591 A1    Sep. 28, 2023

(51) Int. Cl.
| | |
|---|---|
| *H05K 5/00* | (2006.01) |
| *A61B 5/00* | (2006.01) |
| *H01F 7/02* | (2006.01) |
| *H05K 5/02* | (2006.01) |

(52) U.S. Cl.
CPC .............. *A61B 5/6801* (2013.01); *H01F 7/02* (2013.01); *H05K 5/0217* (2013.01); *A61B 2562/164* (2013.01)

(58) Field of Classification Search
CPC .......................... H05K 5/0217; H05K 5/0017
USPC ........................ 361/807, 809, 810, 755, 761
See application file for complete search history.

(56) References Cited

U.S. PATENT DOCUMENTS

| | | | | |
|---|---|---|---|---|
| 2011/0233272 | A1* | 9/2011 | Yau | B42D 3/12 |
| | | | | 235/375 |
| 2020/0352046 | A1* | 11/2020 | Kim | H04M 1/0268 |

\* cited by examiner

*Primary Examiner* — Hung S. Bui
(74) *Attorney, Agent, or Firm* — FOLEY & LARDNER LLP

(57) ABSTRACT

An electronic device is provided. The electronic device includes a flexible body having a first portion and a second portion, an electronic component in the first portion and the second portion of the flexible body, a first magnetic element in the first portion of the flexible body and a second magnetic element in the second portion of the flexible body. The first magnetic and the second magnetic generate a repulsive force with each other when the flexible body is bent and the first portion and the second portion of the flexible body are moved toward each other.

18 Claims, 16 Drawing Sheets

ELECTRONIC DEVICE WITH MAGNETIC ASSEMBLY

BACKGROUND

1. Field of the Disclosure

The instant disclosure relates to, amongst other things, an electronic device with a magnetic assembly. The magnetic assembly is configured to restrict the electronic device from being excessively bent.

2. Description of Related Art

Monitoring biologically-relevant information helps determine a wide array of an individual's physiological characteristics. Integrating a monitoring device (such as a sensor) with a wearable device (such as a wearable patch) allows pertinent information to be collected in a continuous and nonintrusive manner, and thus become increasingly popular.

Such electronic device (integrating a monitoring device with a wearable device) is configured to be attached to a skin of the user. Since the skin of the user may have a curved surface, the electronic device may be bent to conform the curved surface of the skin of the user when the electronic device is attached to the skin of the user. However, the electronic device may include many electronic components therein, and thus the electronic components may be damaged in case the electronic device is excessively bent.

SUMMARY

According to one example embodiment of the instant disclosure, an electronic device includes a bendable body having a first portion and a second portion and an electronic component located at the first portion and the second portion of the bendable body. The first portion and the second portion are configured to repel each other within in a distance.

According to another example embodiment of the instant disclosure, an electronic device includes a main body having a first potion and a second portion, an electronic component disposed in the main body; and a magnetic assembly comprising a first magnetic element in the first portion of the main body and a second magnetic element in the second portion of the main body. The magnetic assembly is configured to resist excessive relative movement between the first portion and the second portion of the main body that is configured to damage the electronic component.

According to another example embodiment of the instant disclosure, an electronic device includes a bendable body having a first end and a second end opposite to the first end and defining a first central axis between the first end and the second end, an electronic component disposed in the bendable body, a first magnetic element disposed in the bendable body and closer to the first central axis than the first end and a second magnetic element disposed in the bendable body and closer to the first central axis than the second end.

In order to further understanding of the instant disclosure, the following embodiments are provided along with illustrations to facilitate appreciation of the instant disclosure; however, the appended drawings are merely provided for reference and illustration, and do not limit the scope of the instant disclosure.

BRIEF DESCRIPTION OF THE DRAWINGS

Aspects of some embodiments of the present disclosure are readily understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1A:
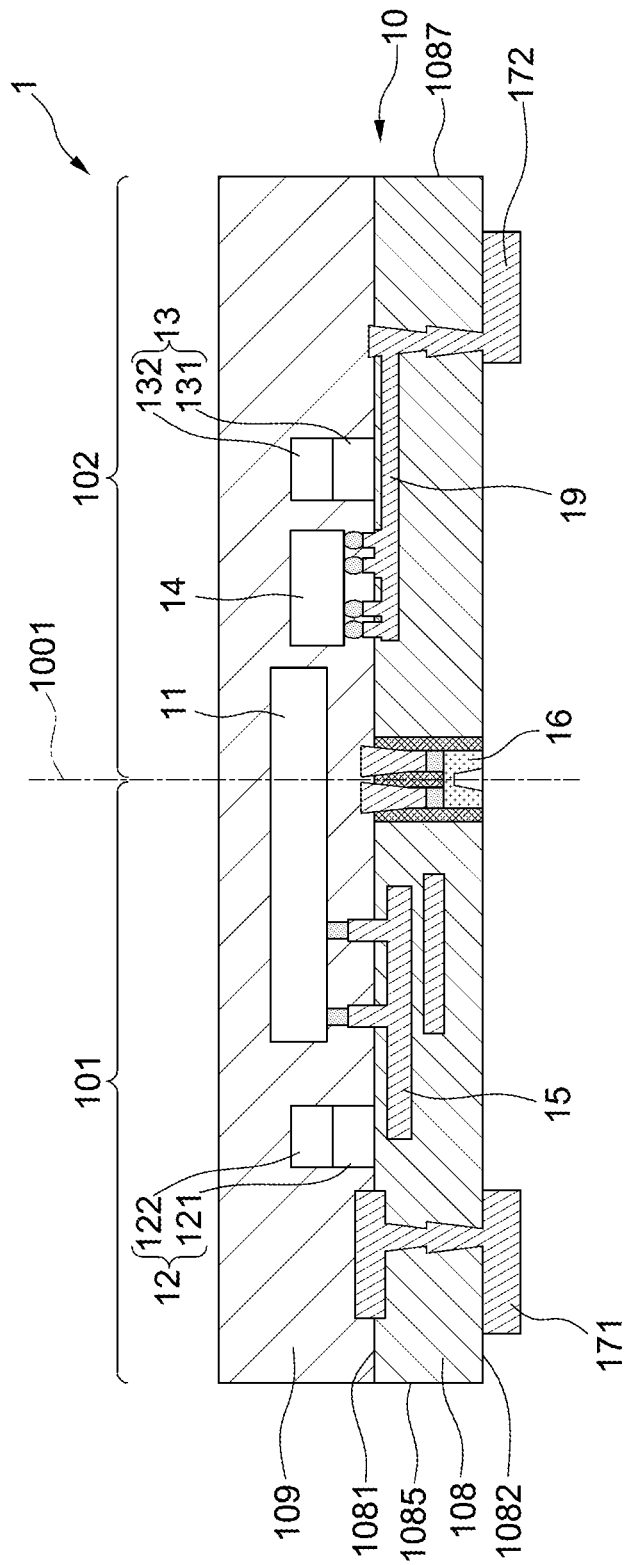
FIG. 1A is a schematic cross-sectional view of an electronic device in accordance with some embodiments of the present disclosure.

Common reference numerals are used throughout the drawings and the detailed description to indicate the same or similar components. Embodiments of the present disclosure will be readily understood from the following detailed description taken in conjunction with the accompanying drawings.

The following disclosure provides for many different embodiments, or examples, for implementing different features of the provided subject matter. Specific examples of components and arrangements are described below to explain certain aspects of the present disclosure. These are, of course, merely examples and are not intended to be limiting. For example, the formation of a first feature over or on a second feature in the description that follows may include embodiments in which the first and second features are formed or disposed in direct contact, and may also include embodiments in which additional features are formed or disposed between the first and second features, such that the first and second features are not in direct contact. In addition, the present disclosure may repeat reference numerals and/or letters in the various examples. This repetition is for the purpose of simplicity and clarity and does not in itself dictate a relationship between the various embodiments and/or configurations discussed.

As used herein, spatially relative terms, such as "beneath," "below," "above," "over," "on," "upper," "lower," "left," "right," "vertical," "horizontal," "side" and the like, may be used herein for ease of description to describe one element or feature's relationship to another element(s) or feature(s) as illustrated in the Figures. The spatially relative terms are intended to encompass different orientations of the device in use or operation in addition to the orientation depicted in the Figures. The device may be otherwise oriented (rotated 90 degrees or at other orientations) and the spatially relative descriptors used herein may likewise be interpreted accordingly. It should be understood that when an element is referred to as being "connected to" or "coupled to" another element, it may be directly connected to or coupled to the other element, or intervening elements may be present.

Present disclosure provides an electronic device with magnetic elements. When the electronic device is bent, the magnetic elements generate a repulsive force with each other so as to restrict the electronic device from being excessively bent.

FIG. 1A is a schematic cross-sectional view of an electronic device 1 in accordance with some embodiments of the present disclosure. The electronic device 1 may be a wearable device, a portable device, a medical monitoring device, or any similar device(s). The electronic device 1 may include a flexible body 10, interconnection structures 15, 19, electronic components 11, 14, magnetic elements 12, 13 and sensing elements 16, 171, 172.

The flexible body 10 may include a substrate 108 (e.g., a carrier) and a protection layer 109. The substrate 108 may have a surface 1081 (e.g., an upper surface) and a surface 1082 (e.g., a lower surface) opposite thereto. The substrate 108 may be pliable. For example, the outline of the substrate 108 may be bendable, twistable, and/or stretchable. The substrate 108 may include a pliable material, a flexible material, or a soft material. The substrate 108 may include, but is not limited to, silicone or rubber. The substrate 108 may include a conductive layer coating on the surface 1081 and/or the surface 1082. The conductive layer of the substrate 108 may have a pattern. The conductive layer of the substrate 108 may be thin enough to be pliable.

The interconnection structures 15 and 19 may be disposed in the substrate 108. The interconnection structure 15, 19 may include a conductive pad disposed on the surface 1081 of the substrate 108. The interconnection structure 15, 19 may include a conductive pillar extending through the substrate 108. The interconnection structure 15, 19 may be configured to electrically connect the elements of the electronic device 1, for example, the electronic components 11, 14 and/or the sensing elements 171, 172. The interconnection structure 15, 19 may include conductive material such as a metal or metal alloy. Examples include gold (Au), silver (Ag), aluminum (Al), copper (Cu), or an alloy thereof.

The electronic components 11 and 14 may be disposed on the surface 1081 of the substrate 108. The sensing elements 171 and 172 may be disposed on or adjacent to the surface 1082 of the substrate 108. Alternatively, the sensing elements 171 and 172 may be integrated within the substrate 108. The electronic component 14 may be electrically connected to the sensing elements 171 and 172 through the interconnection structures 15 and 19.

The sensing element 171, 172 may be configured to detect a biosignal. The biosignal may include: a pulse travel time (PTT), an electroencephalogram (EEG), electrocardiogram (ECG), electromyogram (EMG), heart rate variability (HRV), oxygen saturation (unit: $SpO_2$), temperature, or other. As shown in FIG. 1A, a portion of the first sensing element 171 and a portion of the second sensing element 172 are underneath a lower surface of the substrate 108 and configured to detect a biosignal signal of a user.

The electronic component 14 may be configured to receive the biosignal from the sensing element 171, 172. The electronic component 14 may be configured to process the biosignal to generate a processed data. In some embodiments, the electronic component 14 may be configured to amplify the biosignal. In some embodiments, the electronic component 14 may be configured to convert the biosignal or the amplified biosignal into digital data for the subsequent processing. The electronic component 14 may be configured to store the processed data. The electronic component 14 may be configured to transmit the processed data to an external device via attached wiring or wirelessly. The electronic component 14 may include a system-in-package (SiP). The electronic component 14 may include one or more dies.

In some embodiments, the sensing element 171, 172 may be configured to receive or detect an electrical signal representing the received or detected biosignal. The sensing element 171, 172 may be configured to transmit the electrical signal to the electronic component 14 through the interconnection structures 15, 19. The electronic component 14 may be configured to process, store, and/or transmit the electrical signal. In some embodiments, the electronic device 1 may include a plurality of sensing elements, each of which may receive or detect different biosignals, different electrical signals, different thermal signals, or different optical signals.

The electronic component 14 may include a microcontroller, a sensor, a memory, or a wireless transmission module utilizing, for example, Bluetooth or Bluetooth Low Energy (BLE) protocols. The wireless transmission module may transmit the detected biosignal to an external processor. In an alternative embodiment, the electronic component 14 may process the detected biosignal. The electronic component 14 may determine, based on the processed biosignal, to send an alarm message to a device (e.g., an earphone, a mobile phone, or a watch) associated with the electronic device 1.

As shown in FIG. 1A, the sensing element 171, 172 may be exposed from the surface 1082 of the substrate 108. The sensing element 171, 172 may be in contact with or close to subject's skin when the electronic device 1 is worn. The sensing element 171, 172 may include a conductive pad. The sensing element 171, 172 may include an electrode for electrical transmission or thermal transmission. The sensing element 171, 172 may include a conductive material such as a metal, e.g., copper (Cu), gold (Au), silver (Ag), aluminum (Al), titanium (Ti), or the like. The conductive material of the sensing element 171, 172 may include a conductive silicone, a thermal conductive silicone, a conductive rubber, a conductive sponge, a conductive fabric, or a conductive fiber.

In some embodiments of the present discourse, the electronic component 11 includes a battery element. The battery element may be configured to supply power to the electronic component 11 and/or the sensing element 16. The battery element may be electrically connected to the electronic component 11. In some embodiments of the present disclosure, the battery element may be configured to be charged through wireless charging. The battery element may include a Li-ion battery.

The sensing element 16 may be disposed in the substrate 108. The sensing element 16 may be configured to detect a biosignal. The biosignal may include a PTT, an EEG, ECG, EMG, HRV, oxygen saturation (unit: $SpO_2$), temperature, or others. The electronic component 14 may be configured to receive the biosignal from the sensing element 16.

As shown in FIG. 1A, the magnetic elements 12 and 13 are disposed on the surface 1082 of the substrate 108. Referring to FIG. 1A, the substrate 18 may include an end 1085 and an end 1087 opposite to the end 1085. In some embodiments of the present disclosure, a horizontal distance between the end 1087 of the substrate 108 and the magnetic element 12 is greater than a horizontal distance between the end 1085 of the substrate 108 and the magnetic element 12, and a horizontal distance between the end 1085 of the substrate 108 and the magnetic element 13 is greater than the end 1087 of the substrate 108 and the magnetic element 13. That is, the magnetic element 12 may be positioned to be close to the end 1085 and far away from the end 1087. The magnetic element 13 may be positioned to be close to the end 1087 and far away from the end 1085.

Referring to FIG. 1A, the magnetic elements 12 may overlap the interconnection structure 15 in a direction substantially perpendicular to the surface 1081/surface 1082 of the substrate 108 (e.g., a vertical direction) and the magnetic elements 13 may overlap the interconnection structure 19 in a direction substantially perpendicular to the surface 1081/surface 1082 of the substrate 108 (e.g., the vertical direction). The magnetic 12 and 13 may not overlap the sensing element 171, 172 in the direction substantially perpendicular to the surface 1081/surface 1082 of the substrate 108 (e.g., the vertical direction).

The magnetic element 12 may have an end portion 121 facing the surface 1081 of the substrate 108 and an end portion 122 facing away from the surface 1081 of the substrate 108, and the magnetic element 13 may have an end portion 131 facing the surface 1081 of the substrate 108 and an end portion 132 facing away from the surface 1081 of the substrate 108. A magnetic polarity of the end portion 121 of the magnetic element 12 may be the same as a magnetic polarity of the end portion 131 of the magnetic element 13, and a magnetic polarity of the end portion 122 of the magnetic element 12 may be the same as a magnetic polarity of the end portion 132 of the magnetic element 13. In some embodiments of the present disclosure, the end portion 121 of the magnetic element 12 includes a magnetic south-pole polarity and the end portion 131 of the magnetic element 13 includes a magnetic south-pole polarity, and the end portion 122 of the magnetic element 12 includes a magnetic north-pole polarity and the end portion 132 of the magnetic element 13 includes a magnetic north-pole polarity.

The protection layer 109 may be disposed on the surface 1081 of the substrate 108. The protection layer 109 may be pliable. For example, the outline of the protection layer 109 may be bendable, twistable, and/or stretchable. The protection layer 109 may cover the electronic components 11 and 14 and the magnetic elements 12 and 13. The protection layer 109 may include a molding compound without fillers. The protection layer 109 may include an encapsulant.

Referring to FIG. 1A, the flexible body 10 of the electronic device 1 may include a first portion 101 and a second portion 102. In some embodiments of the present disclosure, the flexible body 10 of the electronic device is divided into the first portion 101 and the second portion 102 by a centerline 1001 of the flexible body 10. That is, the first portion 101 and the second portion 102 may be connected to each other and a junction of the first portion 101 and the second portion 102 is located at the centerline 1001 of the flexible body 10.

As shown in FIG. 1A, the magnetic element 12 may be disposed in the first portion 101 of the flexible body 10 and the magnetic element 13 may be disposed in the second portion 102 of the flexible body 10. The sensing element 171 may be disposed on the first portion 101 of the flexible body 10 and the sensing element 172 may be disposed on the second portion 102 of the flexible body 10. Moreover, the sensing element 16 may be adjacent to the junction of the first portion 101 and the second portion 102. Further, the electronic component 11 may extend across the centerline 1001 of the flexible body 10. That is, the electronic component 11 may be disposed in the first portion 101 and the second portion 102 of the flexible body 10 and across the junction of the first portion 101 and the second portion 102 of the flexible body 10.

In some embodiments of the present disclosure, a horizontal distance between the centerline 1001 of the flexible body 10 and the magnetic element 12 is substantially equal to a horizontal distance between the centerline 100 of the flexible body 10 and the magnetic element 13. That is, a horizontal distance between the junction of the first portion 101 and the second portion 102 and the magnetic element 12 may be substantially equal to a horizontal distance between the junction of the first portion 101 and the second portion 102 and the magnetic element 13. In some embodiments of the present disclosure, a horizontal distance between the end 1085 of the substrate 108 and the magnetic element 12 is equal to or greater than a horizontal distance between the centerline 1001 of the flexible body 10 and the magnetic element 12. That is, a horizontal distance between the end 1085 of the substrate 108 and the magnetic element 12 may be equal to or greater than a horizontal distance between the junction of the first portion 101 and the second portion 102 and the magnetic element 12. In some embodiments of the present disclosure, a horizontal distance between the end 1087 of the substrate 108 and the magnetic element 13 is equal to or greater than a horizontal distance between the centerline 1001 of the flexible body 10 and the magnetic element 13. That is, a horizontal distance between the end 1087 of the substrate 108 and the magnetic element 13 may be equal to or greater than a horizontal distance between the junction of the first portion 101 and the second portion 102 and the magnetic element 13. In some embodiments of the present disclosure, the horizontal distance between the end 1085 of the substrate 108 and the magnetic element 12 is equal to or smaller than ¾ of a horizontal distance between the end 1085 of the substrate 108 and the centerline 1001 of the flexible body 10. That is, the horizontal distance between the end 1085 of the substrate 108 and the magnetic element 12 may be equal to or smaller than ¾ of a horizontal distance between the end 1085 of the substrate 108 and the junction of the first portion 101 and the second portion 102. In some embodiments of the present disclosure, the horizontal distance between the end 1087 of the substrate 108 and the magnetic element 13 is equal to or smaller than ¾ of a horizontal distance between the end 1087 of the substrate 108 and the centerline 1001 of the flexible body 10. That is, the horizontal distance between the end 1087 of the substrate 108 and the magnetic element 13 may be equal to or smaller than ¾ of a horizontal distance between the end 1087 of the substrate 108 and the junction of the first portion 101 and the second portion 102.

Figure 1B:
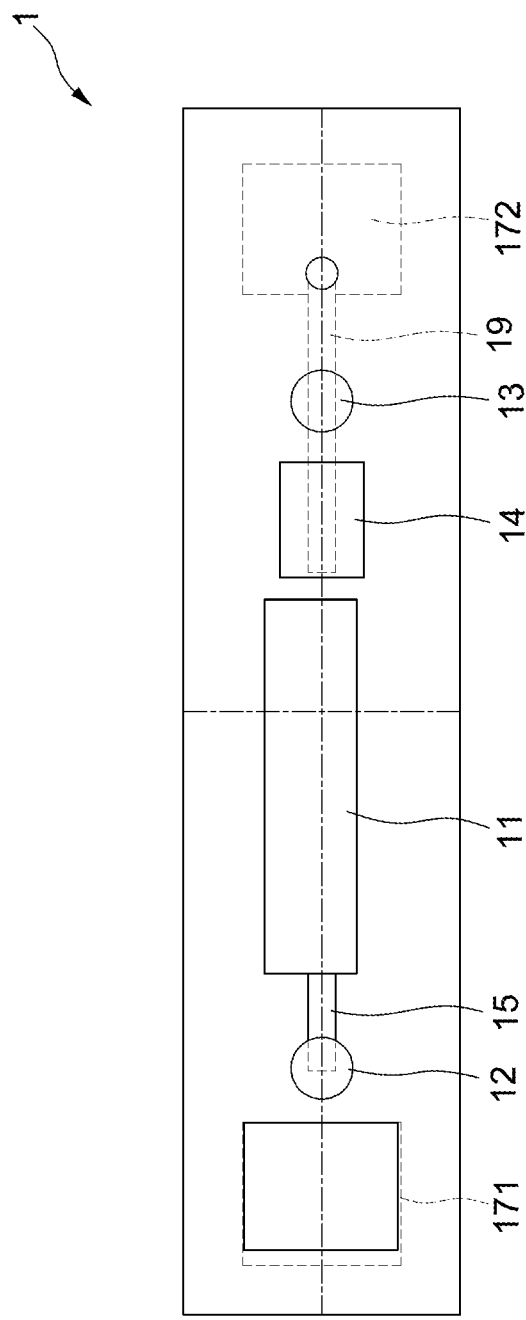
FIG. 1B is a schematic top view of an electronic device in accordance with some embodiments of the present disclosure.

FIG. 1B is a schematic top view of an electronic device in accordance with some embodiments of the present disclosure, in which the protection layer 109 is not shown in FIG. 1B. As shown in FIG. 1B, the magnetic elements 12 may at least partially overlap the interconnection structure 15 and the magnetic elements 13 may at least partially overlap the interconnection structure 19. Further, the magnetic 12 and 13 may not overlap the sensing element 171, 172.

Figure 1C:
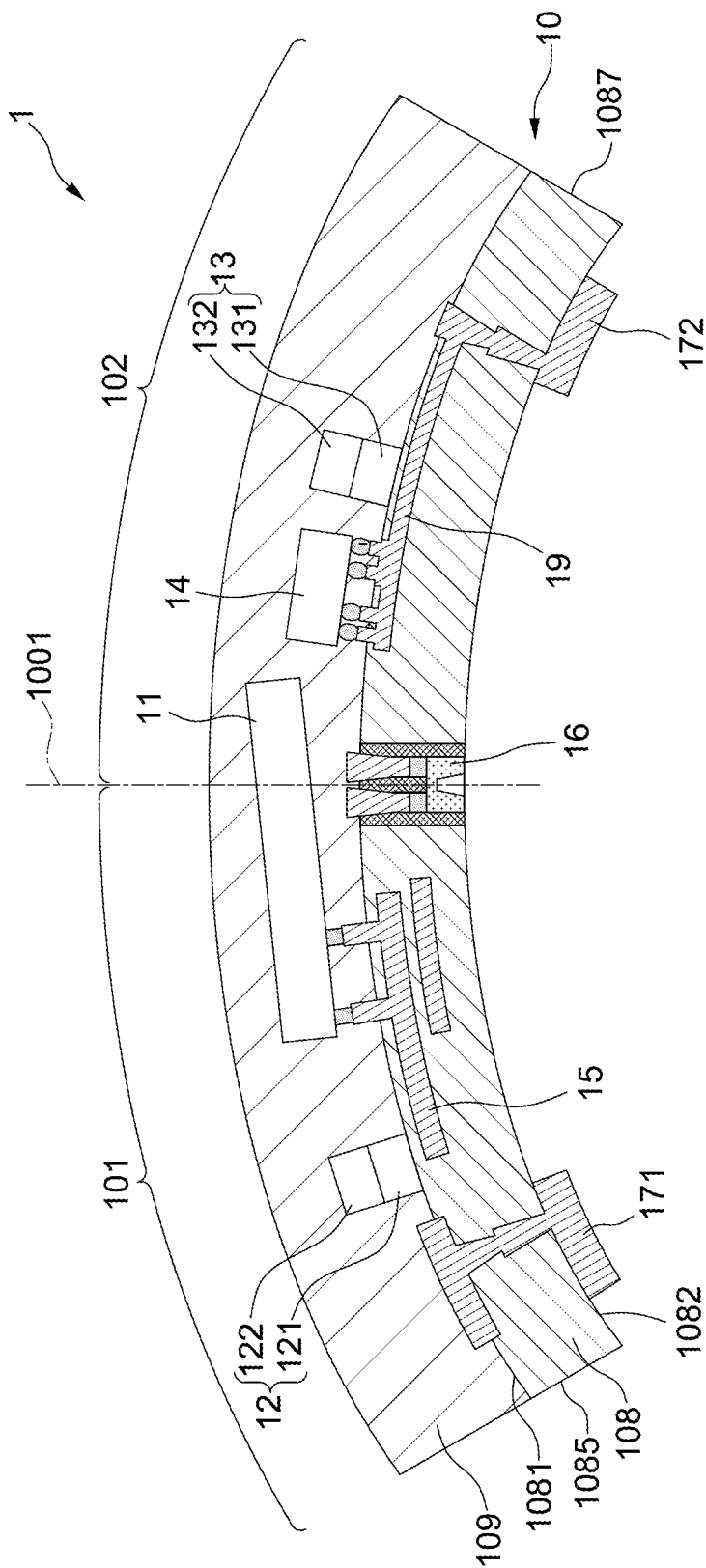
FIG. 1C is a schematic diagram of an electronic device being bent in accordance with some embodiments of the present disclosure.
Figure 1D:
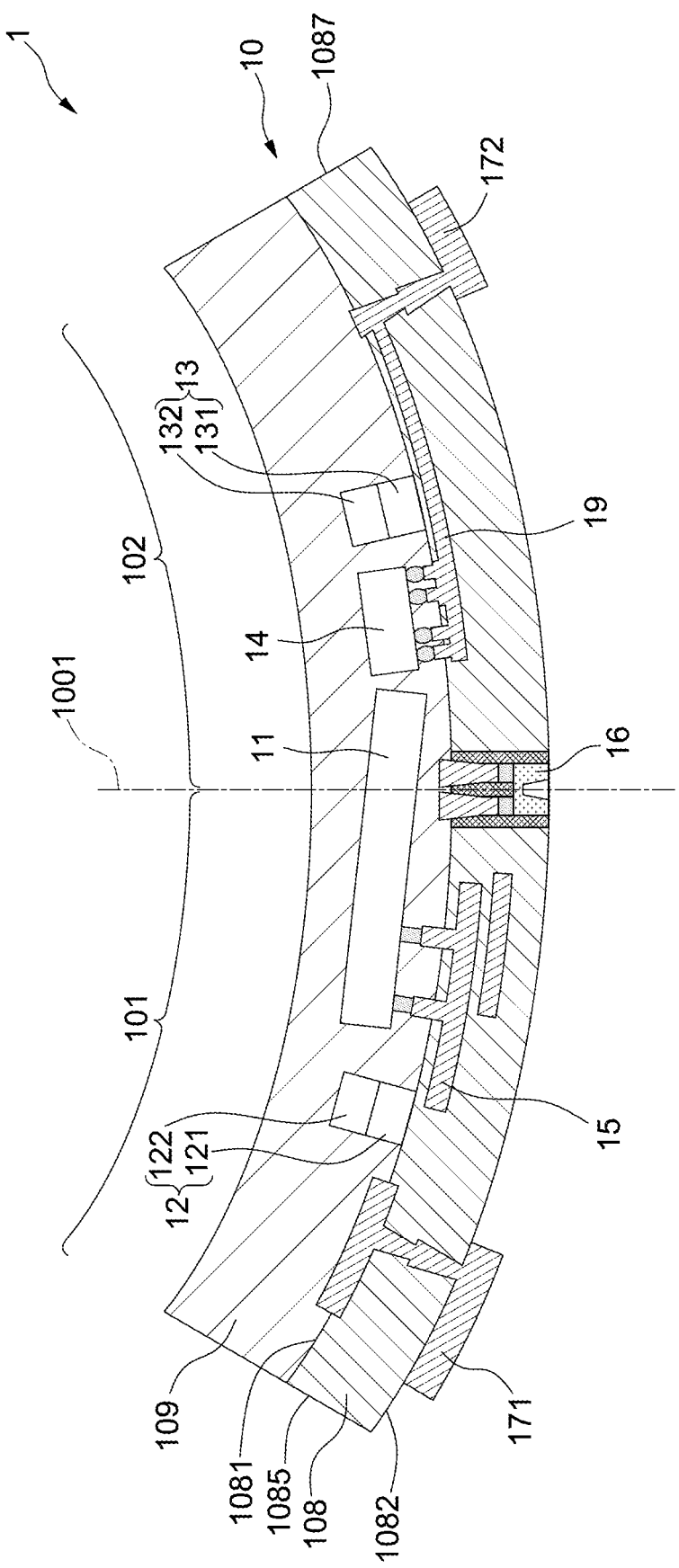
FIG. 1D is a schematic diagram of an electronic device being bent in accordance with some embodiments of the present disclosure.

FIG. 1C and FIG. 1D are schematic diagrams of the electronic device 1 being bent in accordance with some embodiments of the present disclosure. As above mentioned, the substrate 108 and the protection layer 109 of the flexible body 10 of the electronic device 1 is pliable, and thus the flexible body 10 of the electronic device 1 could be bent as shown in FIG. 1C and/or FIG. 1D. The first portion 101 and the second portion 102 of the flexible body could be moved relative to each other when the flexible body 10 of the electronic device 1 is bent. However, there may be many electronic components integrated in the electronic device 1, and thus the electronic components in the electronic device 1 may be damaged or disabled in case the electronic device 1 is excessively bent. Especially, the electronic component 11 which disposed in the first portion 101 and the second portion 102 of the flexible body 10 may be damaged due to the over-bending of the electronic device 1.

Referring to FIG. 1C, the first portion 101 and the second portion 102 are moved toward each other when the flexible body 10 of the electronic device 1 is bent. As shown in FIG. 1C, a lower surface of the first portion 101 and a lower surface of the second portion 102 are moved toward each other, and the end portion 121 of the magnetic element 12 and the end portion 131 of the magnetic element 13 are moved toward each other as well. As above mentioned, the magnetic polarity of the end portion 121 of the magnetic element 12 may be the same as the magnetic polarity of the end portion 131 of the magnetic element 13. Therefore, the magnetic elements 12 and 13 may generate a repulsive force with each other when the end portion 121 of the magnetic element 12 and the end portion 131 of the magnetic element 13 are moved toward each other. Such repulsive force generated by the magnetic elements 12 and 13 may resist the relative movement between the first portion 101 and the second portion 102 and thus may restrict the electronic device 1 from being excessively bent. That is, the electronic component 11 may be prevented from being damaged due to the repulsive force generated by the magnetic elements 12 and 13.

Referring to FIG. 1D, the first portion 101 and the second portion 102 are moved toward each other when the flexible body 10 of the electronic device 1 is bent. As shown in FIG. 1D, an upper surface of the first portion 101 and an upper surface of the second portion 102 are moved toward each other, and the end portion 122 of the magnetic element 12 and the end portion 132 of the magnetic element 13 are moved toward each other as well. As above mentioned, the magnetic polarity of the end portion 122 of the magnetic element 12 may be the same as the magnetic polarity of the end portion 132 of the magnetic element 13. Therefore, the magnetic elements 12 and 13 may generate a repulsive force with each other when the end portion 122 of the magnetic element 12 and the end portion 132 of the magnetic element 13 are moved toward each other. Such repulsive force generated by the magnetic elements 12 and 13 may resist the relative movement between the first portion 101 and the second portion 102 and thus may restrict the electronic device 1 from being excessively bent. That is, the electronic component 11 may be prevented from being damaged due to the repulsive force generated by the magnetic elements 12 and 13.

Figure 1F:
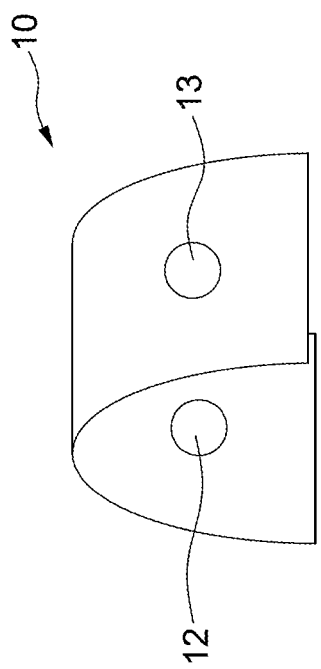
FIG. 1F is a schematic diagram of an electronic device being bent in accordance with some embodiments of the present disclosure.
Figure 1E:
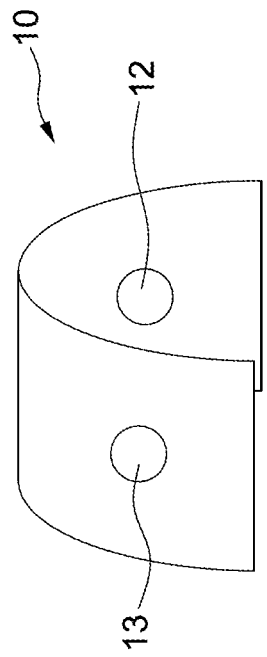
FIG. 1E is a schematic diagram of an electronic device being bent in accordance with some embodiments of the present disclosure.

FIG. 1E and FIG. 1F are schematic diagrams of the electronic device 1 being bent in accordance with some embodiments of the present disclosure. As stated above, when the flexible body 10 is bent and the first portion 101 and the second portion 102 are moved toward each other, the magnetic elements 12 and 13 may generate a repulsive force with each other. As shown in FIG. 1E and FIG. 1F, the repulsive force generated by the magnetic elements 12 and 13 may cause the first portion 101 and the second portion 102 to be in a staggered position relative to one another when the flexible body 10 is bent. That is, the flexible body 10 cannot be bent along a centerline between the first portion 101 and the second portion 102, and such bending may prevent the electronic component 11 from being damaged.

Figure 1G:
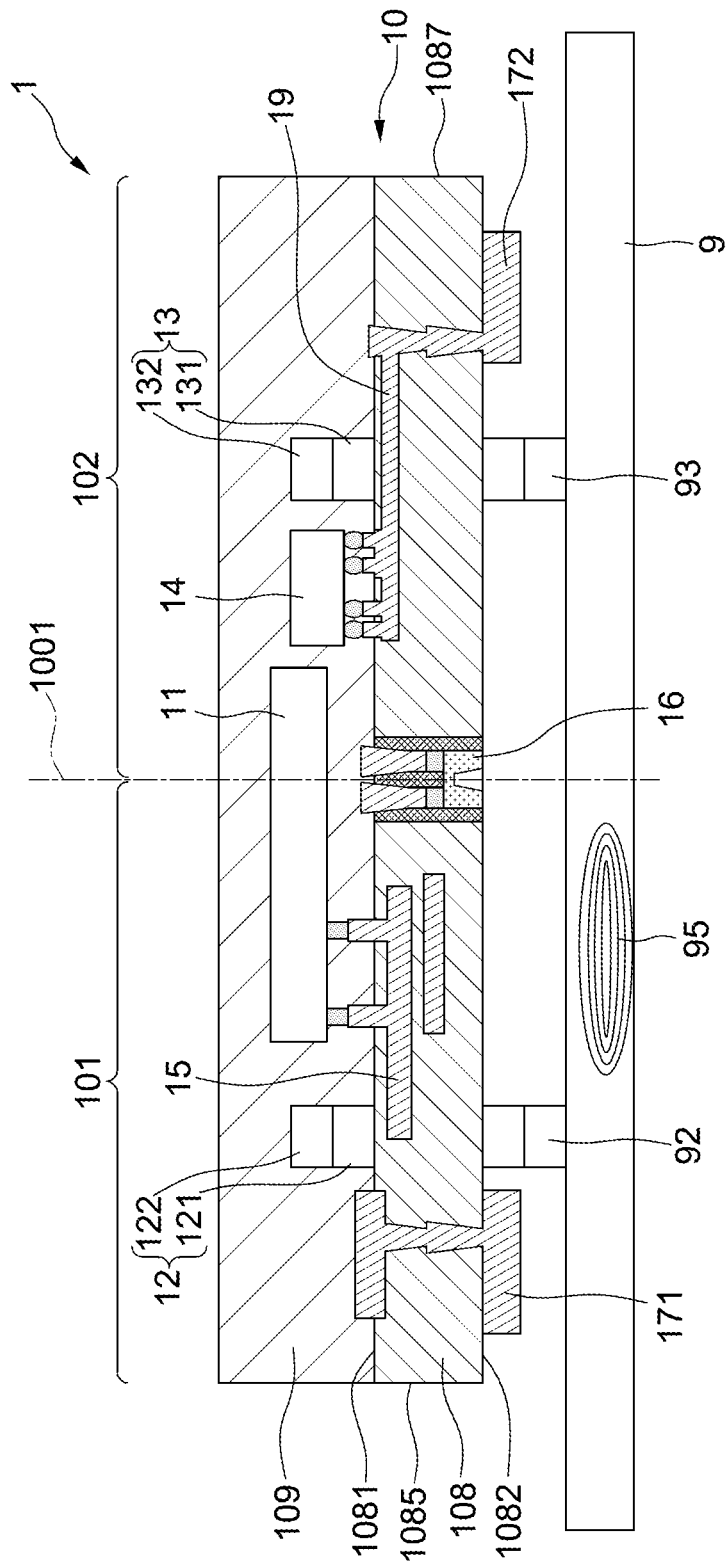
FIG. 1G is a schematic diagram of an electronic device being attached to a stand in accordance with some embodiments of the present disclosure.

FIG. 1G is a schematic diagram of the electronic device being attached to a stand 9 in accordance with some embodiments of the present disclosure. The stand 9 is configured to hold the electronic device 1. In some embodiments of the present disclosure, the stand 9 has fixed members 92 and 93. The fixed members 92 and 93 may substantially align with the magnetic elements 12 and 13 of the electronic device 1 when the electronic device 1 is held by the stand 9. In some embodiments of the present disclosure, the fixed member 92, 93 includes a metal component. In some embodiments of the present disclosure, the fixed member 92, 93 includes a magnetic component. That is, when the electronic device 1 is arranged on the stand 9, the magnetic elements 12 and 13 of the electronic device 1 and the fixed members 92 and 93 of the stand 9 attract each other. Thus, the electronic device 1 is held on the stand 9 firmly.

In some embodiments of the present disclosure, the stand 9 has a charging element 95. When the electronic device 1 is held by the stand 9, the charging element 95 of the stand 9 transmits power wirelessly to the battery component of the electronic device 1.

Figure 2A:
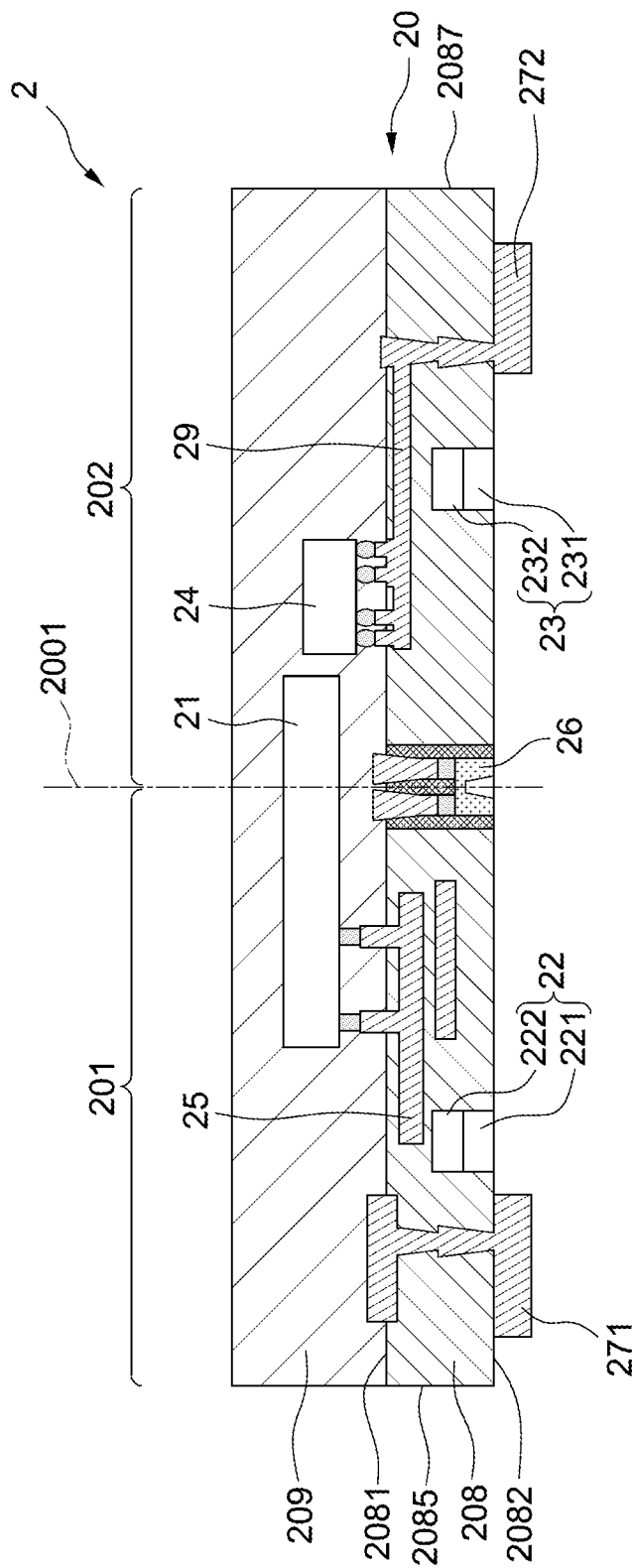
FIG. 2A is a schematic cross-sectional view of an electronic device in accordance with some embodiments of the present disclosure.

FIG. 2A is a schematic cross-sectional view of an electronic device 2 in accordance with some embodiments of the present disclosure. The electronic device 2 may be a wearable device, a portable device, a medical monitoring device, or any similar device(s). The electronic device 2 may include a flexible body 20, interconnection structures 25, 29, electronic components 21, 24, magnetic elements 22, 23 and sensing elements 26, 271, 272.

The flexible body 20 may include a substrate 208 (e.g., a carrier) and a protection layer 209. The substrate 208 may have a surface 2081 (e.g., an upper surface) and a surface 2082 (e.g., a lower surface) opposite thereto. The substrate 208 may be pliable. For example, the outline of the substrate 208 may be bendable, twistable, and/or stretchable. The substrate 208 may include a pliable material, a flexible material, or a soft material. The substrate 208 may include, but is not limited to, silicone or rubber. The substrate 208 may include a conductive layer coating on the surface 2081 and/or the surface 2082. The conductive layer of the substrate 208 may have a pattern. The conductive layer of the substrate 208 may be thin enough to be pliable.

The interconnection structure 25, 29 may be disposed in the substrate 208. The interconnection structure 25, 29 may include a conductive pad disposed on the surface 2081 of the substrate 208. The interconnection structure 25, 29 may include a conductive pillar extending through the substrate 208. The interconnection structure 25, 29 may be configured to electrically connect the elements of the electronic device 2, for example, the electronic components 21, 24 and/or the sensing elements 271, 272. The interconnection structure 25, 29 may include conductive material such as a metal or metal alloy. Examples include gold (Au), silver (Ag), aluminum (Al), copper (Cu), or an alloy thereof.

The electronic components 21 and 24 may be disposed on the surface 2081 of the substrate 208. The sensing elements 271 and 272 may be disposed on or adjacent to the surface 2082 of the substrate 208. Alternatively, the sensing elements 271 and 272 may be integrated within the substrate 208. The electronic component 24 may be electrically connected to the sensing elements 271 and 272 through the interconnection structure 25, 29.

The sensing element 271, 272 may be configured to detect a biosignal. The biosignal may include: a pulse travel time (PTT), an electroencephalogram (EEG), electrocardiogram (ECG), electromyogram (EMG), heart rate variability (HRV), oxygen saturation (unit: $SpO_2$), temperature, or other. As shown in FIG. 2A, a portion of the first sensing element 271 and a portion of the second sensing element 272 are underneath a lower surface of the substrate 208 and configured to detect a biosignal signal of a user.

The electronic component 24 may be configured to receive the biosignal from the sensing element 271, 272. The electronic component 24 may be configured to process the biosignal to generate a processed data. In some embodiments, the electronic component 24 may be configured to amplify the biosignal. In some embodiments, the electronic component 24 may be configured to convert the biosignal or the amplified biosignal into digital data for the subsequent processing. The electronic component 24 may be configured to store the processed data. The electronic component 24 may be configured to transmit the processed data to an external device via attached wiring or wirelessly. The electronic component 24 may include a system-in-package (SiP). The electronic component 24 may include one or more dies.

In some embodiments, the sensing element 271, 272 may be configured to receive or detect an electrical signal representing the received or detected biosignal. The sensing element 271, 272 may be configured to transmit the electrical signal to the electronic component 24 through the interconnection structure 25, 29. The electronic component 24 may be configured to process, store, and/or transmit the electrical signal. In some embodiments, the electronic device 2 may include a plurality of sensing elements, each of which may receive or detect different biosignals, different electrical signals, different thermal signals, or different optical signals.

The electronic component 24 may include a microcontroller, a sensor, a memory, or a wireless transmission module utilizing, for example, Bluetooth or Bluetooth Low Energy (BLE) protocols. The wireless transmission module may transmit the detected biosignal to an external processor. In an alternative embodiment, the electronic component 14 may process the detected biosignal. The electronic component 24 may determine, based on the processed biosignal, to send an alarm message to a device (e.g., an earphone, a mobile phone, or a watch) associated with the electronic device 2.

As shown in FIG. 2A, the sensing element 271, 272 may be exposed from the surface 2082 of the substrate 208. The sensing element 271, 272 may be in contact with or close to subject's skin when the electronic device 2 is worn. The sensing element 271, 272 may include a conductive pad. The sensing element 271, 272 may include an electrode for electrical transmission or thermal transmission. The sensing element 271, 272 may include a conductive material such as a metal, e.g., copper (Cu), gold (Au), silver (Ag), aluminum (Al), titanium (Ti), or the like. The conductive material of the sensing element 271, 272 may include a conductive silicone, a thermal conductive silicone, a conductive rubber, a conductive sponge, a conductive fabric, or a conductive fiber.

In some embodiments of the present discourse, the electronic component 21 includes a battery element. The battery element may be configured to supply power to the electronic component 21 and/or the sensing element 26. The battery element may be electrically connected to the electronic component 21. In some embodiments of the present disclosure, the battery element may be configured to be charged through wireless charging. The battery element may include a Li-ion battery.

The sensing element 26 may be disposed in the substrate 208. The sensing element 26 may be configured to detect a biosignal. The biosignal may include a PTT, an EEG, ECG, EMG, HRV, oxygen saturation (unit: $SpO_2$), temperature, or others. The electronic component 24 may be configured to receive the biosignal from the sensing element 26.

As shown in FIG. 2A, the magnetic elements 22 and 23 are disposed in the substrate 208. Referring to FIG. 2A, the substrate 28 may include an end 2085 and an end 2087 opposite to the end 2085. In some embodiments of the present disclosure, a horizontal distance between the end 2087 of the substrate 208 and the magnetic element 22 is greater than a horizontal distance between the end 2085 of the substrate 208 and the magnetic element 22, and a horizontal distance between the end 2085 of the substrate 208 and the magnetic element 23 is greater than the end 2087 of the substrate 208 and the magnetic element 23. That is, the magnetic element 22 may be positioned to be close to the end 2085 and far away from the end 2087. The magnetic element 23 may be positioned to be close to the end 2087 and far away from the end 2085.

Referring to FIG. 2A, the magnetic elements 22 may overlap the interconnection structure 25 in a direction substantially perpendicular to the surface 2081/surface 2082 of the substrate 208 (e.g., a vertical direction), and the magnetic elements 23 may overlap the interconnection structure 29 in a direction substantially perpendicular to the surface 2081/surface 2082 of the substrate 208 (e.g., the vertical direction). The magnetic 12 and 13 may not overlap the sensing element 271, 272 in the direction substantially perpendicular to the surface 2081/surface 2082 of the substrate 208 (e.g., the vertical direction). The magnetic 12 and 13 may not overlap the electronic component 11, 14 in the direction substantially perpendicular to the surface 2081/surface 2082 of the substrate 208 (e.g., the vertical direction). In some embodiments of the present disclosure, the magnetic 12 and 13 overlaps the electronic component, which is disposed on the substrate 208 and free from being magnetically affected, in the direction substantially perpendicular to the surface 2081/surface 2082 of the substrate 208 (e.g., the vertical direction).

The magnetic element 22 may have an end portion 221 facing the surface 2082 of the substrate 208 and an end portion 222 facing away from the surface 2082 of the substrate 208, and the magnetic element 23 may have an end portion 231 facing the surface 2082 of the substrate 208 and an end portion 232 facing away from the surface 2081 of the substrate 208. A magnetic polarity of the end portion 221 of the magnetic element 22 may be the same as a magnetic polarity of the end portion 231 of the magnetic element 23, and a magnetic polarity of the end portion 222 of the magnetic element 22 may be the same as a magnetic polarity of the end portion 232 of the magnetic element 23. In some embodiments of the present disclosure, the end portion 221 of the magnetic element 22 includes a magnetic south-pole polarity and the end portion 231 of the magnetic element 23 includes a magnetic south-pole polarity, and the end portion 222 of the magnetic element 22 includes a magnetic north-pole polarity and the end portion 232 of the magnetic element 23 includes a magnetic north-pole polarity.

The protection layer 209 may be disposed on the surface 2081 of the substrate 208. The protection layer 209 may be pliable. For example, the outline of the protection layer 209 may be bendable, twistable, and/or stretchable. The protection layer 209 may cover the electronic components 21 and 24. The protection layer 209 may include a molding compound without fillers. The protection layer 209 may include an encapsulant.

Referring to FIG. 2A, the flexible body 20 of the electronic device 1 may include a first portion 201 and a second portion 202. In some embodiments of the present disclosure, the flexible body 20 of the electronic device 2 is divided into the first portion 201 and the second portion 202 by a centerline 2001 of the flexible body 20. That is, the first portion 201 and the second portion 202 may be connected to each other and a junction of the first portion 201 and the second portion 202 is located at the centerline 2001 of the flexible body 20.

As shown in FIG. 2A, the magnetic element 22 may be disposed in the first portion 201 of the flexible body 20 and the magnetic element 23 may be disposed in the second portion 202 of the flexible body 20. The sensing element 271 may be disposed on the first portion 201 of the flexible body 20 and the sensing element 272 may be disposed on the second portion 202 of the flexible body 20. Moreover, the sensing element 16 may be adjacent to the junction of the first portion 201 and the second portion 202. Further, the electronic component 21 may extend across the centerline 2001 of the flexible body 20. That is, the electronic component 21 may be disposed in the first portion 201 and the second portion 202 of the flexible body 20 and across the junction of the first portion 201 and the second portion 202 of the flexible body 20.

In some embodiments of the present disclosure, a horizontal distance between the centerline 2001 of the flexible body 20 and the magnetic element 22 is substantially equal to a horizontal distance between the centerline 200 of the flexible body 20 and the magnetic element 23. That is, a horizontal distance between the junction of the first portion 201 and the second portion 202 and the magnetic element 22 may be substantially equal to a horizontal distance between the junction of the first portion 201 and the second portion 202 and the magnetic element 23. In some embodiments of the present disclosure, a horizontal distance between the end 2085 of the substrate 208 and the magnetic element 22 is equal to or greater than a horizontal distance between the centerline 2001 of the flexible body 20 and the magnetic element 22. That is, a horizontal distance between the end 2085 of the substrate 208 and the magnetic element 22 may be equal to or greater than a horizontal distance between the junction of the first portion 201 and the second portion 202 and the magnetic element 22. In some embodiments of the present disclosure, a horizontal distance between the end 2087 of the substrate 208 and the magnetic element 23 is equal to or greater than a horizontal distance between the centerline 2001 of the flexible body 20 and the magnetic element 23. That is, a horizontal distance between the end 2087 of the substrate 208 and the magnetic element 23 may be equal to or greater than a horizontal distance between the junction of the first portion 201 and the second portion 202 and the magnetic element 23. In some embodiments of the present disclosure, the horizontal distance between the end 2085 of the substrate 208 and the magnetic element 22 is equal to or smaller than ¾ of a horizontal distance between the end 2085 of the substrate 208 and the centerline 2001 of the flexible body 20. That is, the horizontal distance between the end 2085 of the substrate 208 and the magnetic element 22 may be equal to or smaller than ¾ of a horizontal distance between the end 2085 of the substrate 208 and the junction of the first portion 201 and the second portion 202. In some embodiments of the present disclosure, the horizontal distance between the end 2087 of the substrate 208 and the magnetic element 23 is equal to or smaller than ¾ of a horizontal distance between the end 2087 of the substrate 208 and the centerline 2001 of the flexible body 20. That is, the horizontal distance between the end 2087 of the substrate 208 and the magnetic element 23 may be equal to or smaller than ¾ of a horizontal distance between the end 2087 of the substrate 208 and the junction of the first portion 201 and the second portion 202.

Figure 2B:
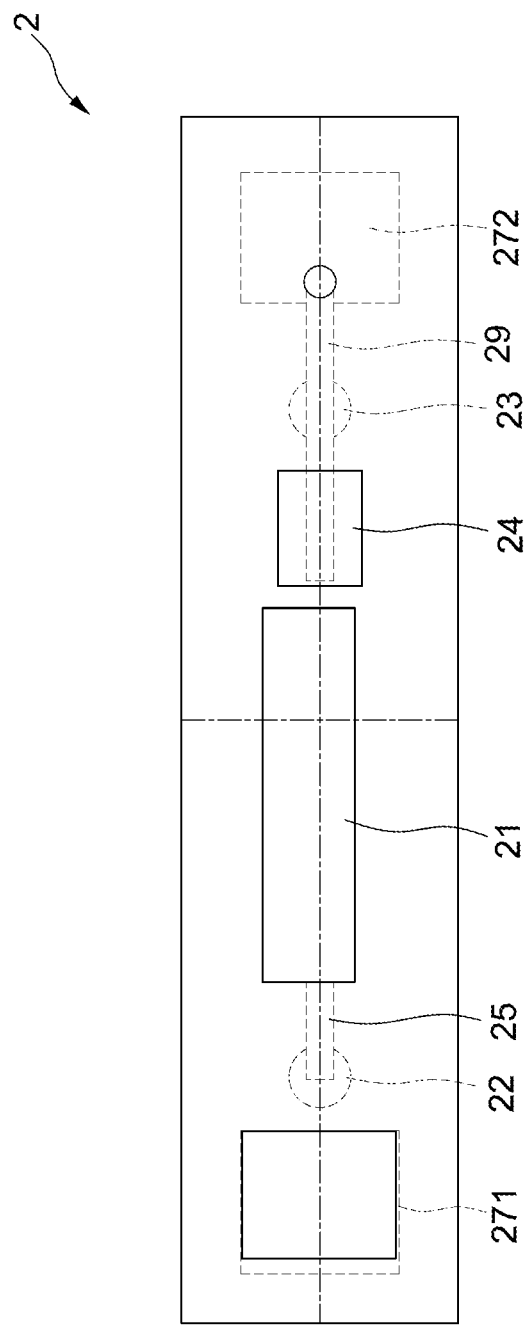
FIG. 2B is a schematic top view of an electronic device in accordance with some embodiments of the present disclosure.

FIG. 2B is a schematic top view of an electronic device in accordance with some embodiments of the present disclosure, in which the protective layer 209 is not shown in FIG. 2B. As shown in FIG. 2B, the magnetic elements 22 may at least partially overlap the interconnection structure 25 and the magnetic elements 23 may at least partially overlap the interconnection structure 29. Further, the magnetic 22 and 23 may not overlap the sensing element 271, 272.

Figure 2C:
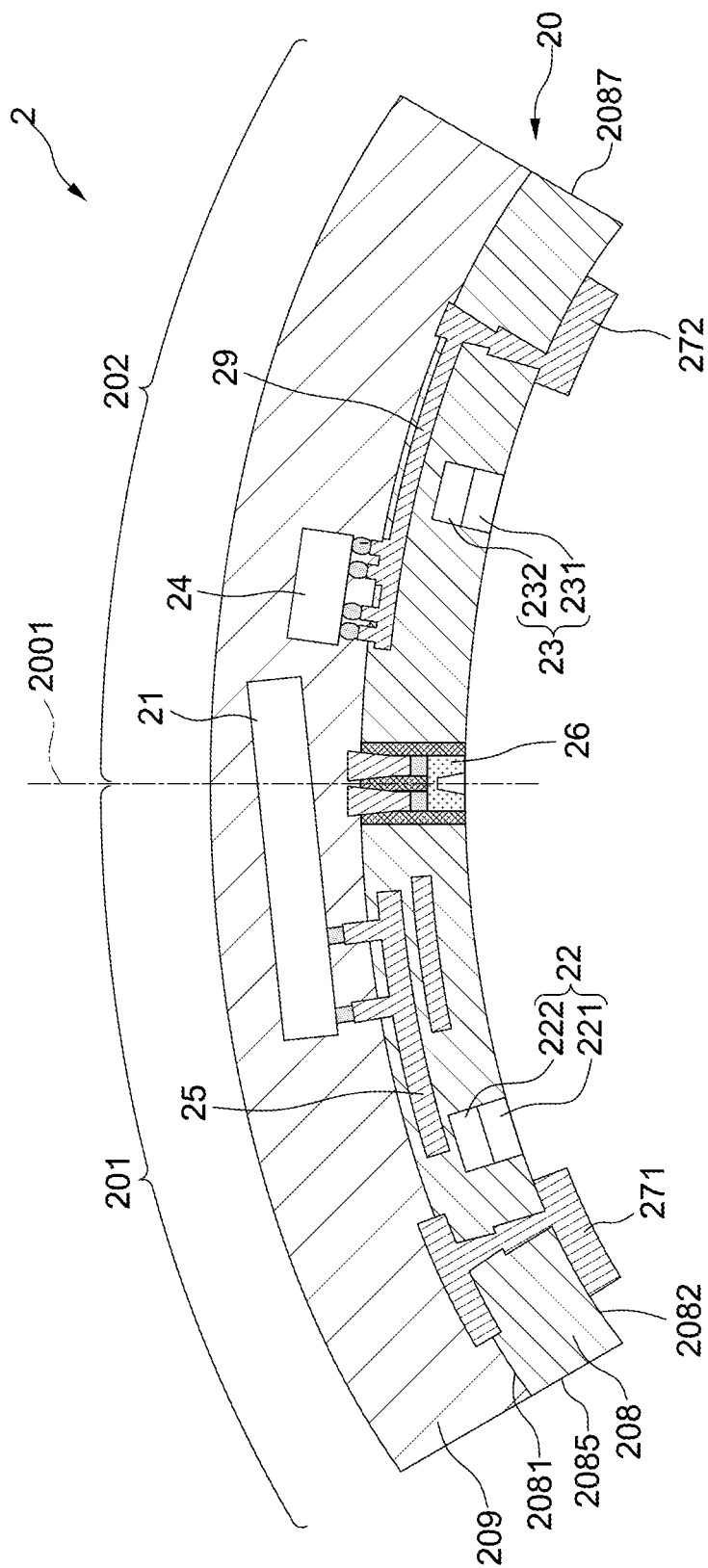
FIG. 2C is a schematic diagram of an electronic device being bent in accordance with some embodiments of the present disclosure.
Figure 2D:
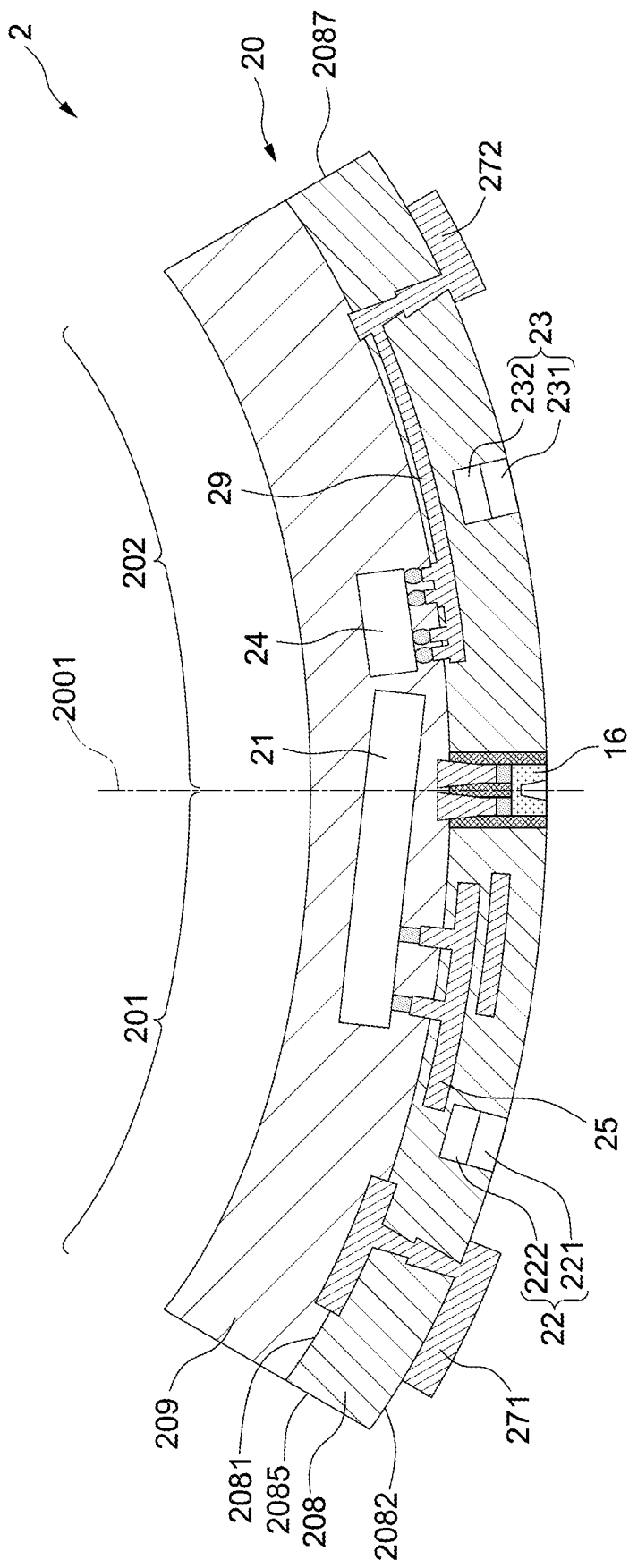
FIG. 2D is a schematic diagram of an electronic device being bent in accordance with some embodiments of the present disclosure.

FIG. 2C and FIG. 2D are schematic diagrams of the electronic device 2 being bent in accordance with some embodiments of the present disclosure. As above mentioned, the substrate 208 and the protection layer 209 of the flexible body 20 of the electronic device 2 is pliable, and thus the flexible body 20 of the electronic device 2 could be bent as shown in FIG. 2C and/or FIG. 2D. The first portion 201 and the second portion 202 of the flexible body 20 could be moved relative to each other when the flexible body 20 of the electronic device 2 is bent. However, there may be many electronic components integrated in the electronic device 2, and thus the electronic components in the electronic device 2 may be damaged or disabled in case the electronic device 2 is excessively bent. Especially, the electronic component 21 which disposed in the first portion 201 and the second portion 202 of the flexible body 20 may be damaged due to the over-bending of the electronic device 2.

Referring to FIG. 2C, the first portion 201 and the second portion 202 are moved toward each other when the flexible body 20 of the electronic device 2 is bent. As shown in FIG. 2C, a lower surface of the first portion 201 and a lower surface of the second portion 202 are moved toward each other, and the end portion 221 of the magnetic element 22 and the end portion 231 of the magnetic element 23 are moved toward each other as well. As above mentioned, the magnetic polarity of the end portion 221 of the magnetic element 22 may be the same as the magnetic polarity of the end portion 231 of the magnetic element 23. Therefore, the magnetic elements 22 and 23 may generate a repulsive force with each other when the end portion 221 of the magnetic element 22 and the end portion 231 of the magnetic element 23 are moved toward each other. Such repulsive force generated by the magnetic elements 22 and 23 may resist the relative movement between the first portion 201 and the second portion 202 and thus may restrict the electronic device 2 from being excessively bent. That is, the electronic component 21 may be prevented from being damaged due to the repulsive force generated by the magnetic elements 22 and 23.

Referring to FIG. 2D, the first portion 201 and the second portion 202 are moved toward each other when the flexible body 20 of the electronic device 2 is bent. As shown in FIG. 2D, an upper surface of the first portion 201 and an upper surface of the second portion 202 are moved toward each other, and the end portion 222 of the magnetic element 22 and the end portion 232 of the magnetic element 23 are moved toward each other as well. As above mentioned, the magnetic polarity of the end portion 222 of the magnetic element 22 may be the same as the magnetic polarity of the end portion 232 of the magnetic element 23. Therefore, the magnetic elements 22 and 23 may generate a repulsive force with each other when the end portion 222 of the magnetic element 22 and the end portion 232 of the magnetic element 23 are moved toward each other. Such repulsive force generated by the magnetic elements 22 and 23 may resist the relative movement between the first portion 201 and the second portion 202 and thus may restrict the electronic device 2 from being excessively bent. That is, the electronic component 21 may be prevented from being damaged due to the repulsive force generated by the magnetic elements 22 and 23.

Figure 2E:
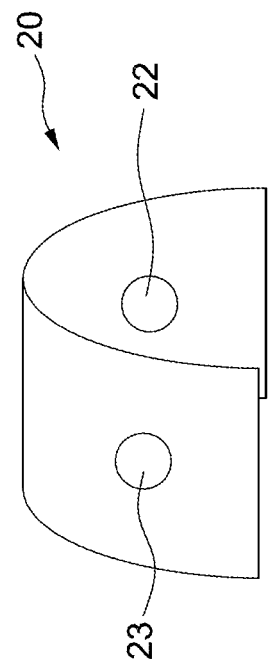
FIG. 2E is a schematic diagram of an electronic device being bent in accordance with some embodiments of the present disclosure.
Figure 2F:
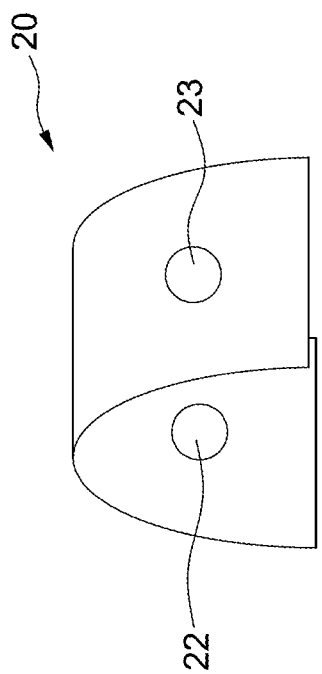
FIG. 2F is a schematic diagram of an electronic device being bent in accordance with some embodiments of the present disclosure.

FIG. 2E and FIG. 2F are schematic diagrams of the electronic device 2 being bent in accordance with some embodiments of the present disclosure. As stated above, when the flexible body 20 is bent and the first portion 201 and the second portion 202 are moved toward each other, the magnetic elements 22 and 23 may generate a repulsive force with each other. As shown in FIG. 2E and FIG. 2F, the repulsive force generated by the magnetic elements 22 and 23 may cause the first portion 201 and the second portion 202 to be in a staggered position relative to one another when the flexible body 20 is bent. That is, the flexible body 20 cannot be bent along a centerline between the first portion 201 and the second portion 202, and such bending may prevent the electronic component 21 from being damaged.

Figure 2G:
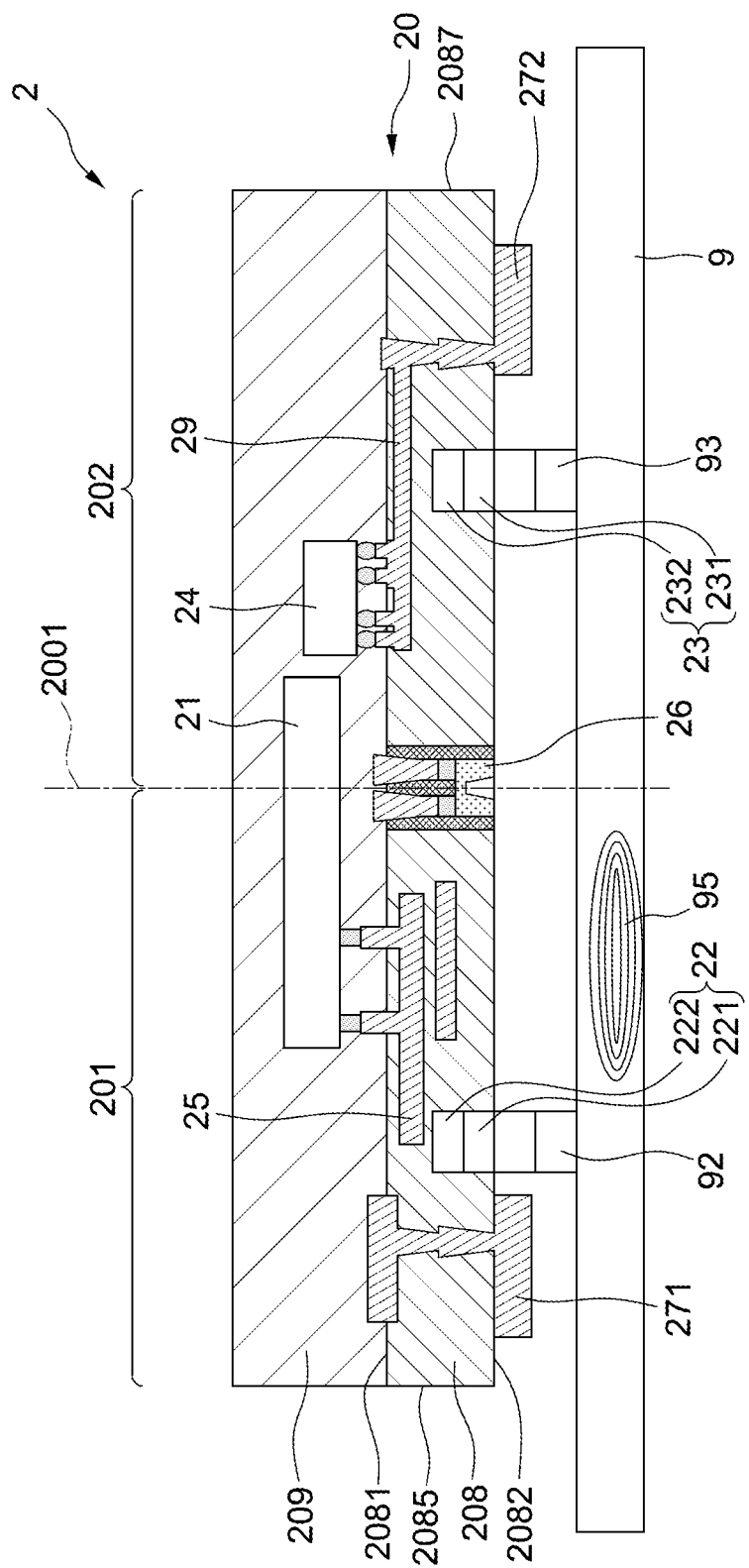
FIG. 2G is a schematic diagram of an electronic device being attached to a stand in accordance with some embodiments of the present disclosure.

FIG. 2G is a schematic diagram of the electronic device 2 being attached to a stand 9 in accordance with some embodiments of the present disclosure. The stand 9 is configured to hold the electronic device 2. In some embodiments of the present disclosure, the stand 9 has fixed members 92 and 93. The fixed members 92 and 93 may substantially align with the magnetic elements 22 and 23 of the electronic device 2 when the electronic device 2 is held by the stand 9. In some embodiments of the present disclosure, the fixed member 92, 93 includes a metal component. In some embodiments of the present disclosure, the fixed member 92, 93 includes a magnetic component. That is, when the electronic device 2 is arranged on the stand 9, the magnetic elements 22 and 23 of the electronic device 2 and the fixed members 92 and 93 of the stand 9 attract each other. Thus, the electronic device 2 is held on the stand 9 firmly.

In some embodiments of the present disclosure, the stand 9 has a charging element 95. When the electronic device 2 is held by the stand 9, the charging element 95 of the stand 9 transmits power wirelessly to the battery component of the electronic device 2.

Figure 3:
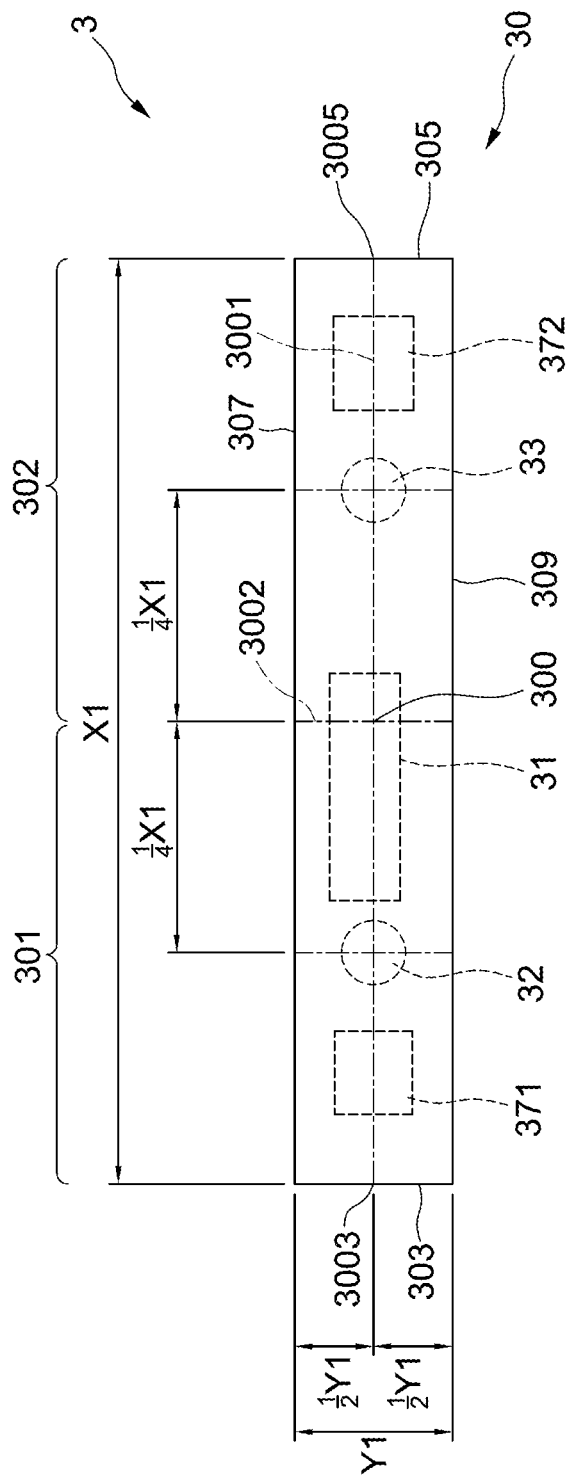
FIG. 3 is a schematic top view of an electronic device in accordance with some embodiments of the present disclosure.

FIG. 3 is a schematic top view of an electronic device 3 in accordance with some embodiments of the present disclosure. In some embodiments of the present disclosure, the electronic device 3 is the same as, or similar to, the electronic device 1 shown in FIG. 1A. In some embodiments of the present disclosure, the electronic device 3 is the same as, or similar to, the electronic device 2 shown in FIG. 2A. Referring to FIG. 3, the electronic device 3 has a flexible body 30. The flexible body 30 may have a geometric shape from a top view perspective. In some embodiments of the present disclosure, the flexible body 30 has a rectangular shape. The geometric shape of the flexible body 30 may define a geometric center 300, a major axis 3001 passing through the geometric center 300 and a minor axis 3002 passing through the geometric center 300 and perpendicular to the major axis 3001. The flexible body 300 of the electronic device 30 may have a first portion 301 and a second portion 302. In some embodiments of the present disclosure, the flexible body 300 is divided into the first portion 301 and the second portion 302 by the minor axis 3002. That is, the first portion 301 and the second portion 302 may be connected to each other and a junction of the first portion 301 and the second portion 302 may be located at the minor axis 3002. The electronic device 30 may have an electronic component 31 disposed in the first portion 301 and the second portion 302 of the flexible body 300. That is, the electronic component 31 may pass across the minor axis 3002.

As shown in FIG. 3, the electronic device 3 may have a magnetic element 32 disposed in the first portion 301 of the flexible body 30 and a magnetic element 33 disposed in the second portion 302 of the flexible body 30. In some embodiments of the present disclosure, the major axis 3001 may substantially pass through the magnetic element 32 and the magnetic element 33 from the top view perspective. In some embodiments of the present disclosure, a horizontal distance between the minor axis 3002 and the magnetic element 32 is substantially equal to a horizontal distance between the minor axis 3002 and the magnetic element 33. In some embodiments of the present disclosure, the horizontal distance between the minor axis 3002 and the magnetic element 32 is substantially equal to a horizontal distance between an end 3003 of the major axis 3001 and the magnetic element 32. In some embodiments of the present disclosure, the end 3003 is an intersection point of the major axis 3001 and a lateral side 303 of the flexible body 30. That is, a horizontal distance between the minor axis 3002 and the magnetic element 32 is substantially equal to a horizontal distance between the end 3003 and the magnetic element 32. Thus, a horizontal distance between the junction of the first portion 301 and 302 and the magnetic element 32 is substantially equal to a horizontal distance between the lateral side 303 of the flexible body 30 and the magnetic element 32. In some embodiments of the present disclosure, the horizontal distance between the minor axis 3002 and the magnetic element 33 is substantially equal to a horizontal distance between an end 3005 of the major axis 3001 and the magnetic element 33. In some embodiments of the present disclosure, the end 3005 is an intersection point of the major axis 3001 and a lateral side 305 of the flexible body 30. That is, a horizontal distance between the minor axis 3002 and the magnetic element 33 is substantially equal to a horizontal distance between the end 3005 and the magnetic element 32. Thus, a horizontal distance between the junction of the first portion 301 and 302 and the magnetic element 33 is substantially equal to a horizontal distance between the lateral side 305 of the flexible body 30 and the magnetic element 33.

Referring to FIG. 3, a distance between the lateral side 303 and the lateral side 305 may be X1, and a distance between the lateral side 307 and the lateral side 309 may be Y1. A distance between the minor axis 3002 and the magnetic element 32 may be ¼ X1, and a distance between the minor axis 3002 and the magnetic element 33 may be ¼ X1. Further, a distance between the lateral side 307 and the magnetic element 32 may be ½ Y1, and a distance between the lateral side 307 and the magnetic element 33 may be ½ Y1, and a distance between the lateral side 309 and the magnetic element 32 may be ½ Y1, and a distance between the lateral side 309 and the magnetic element 33 may be ½ Y1.

In addition, the electronic device 3 may include sensing elements 371 and 372. As shown in FIG. 3, the magnetic element 32 may not overlap the sensing element 371 from a top view perspective, and the magnetic element 33 may not overlap the sensing element 372 from the top view perspective.

Figure 4:
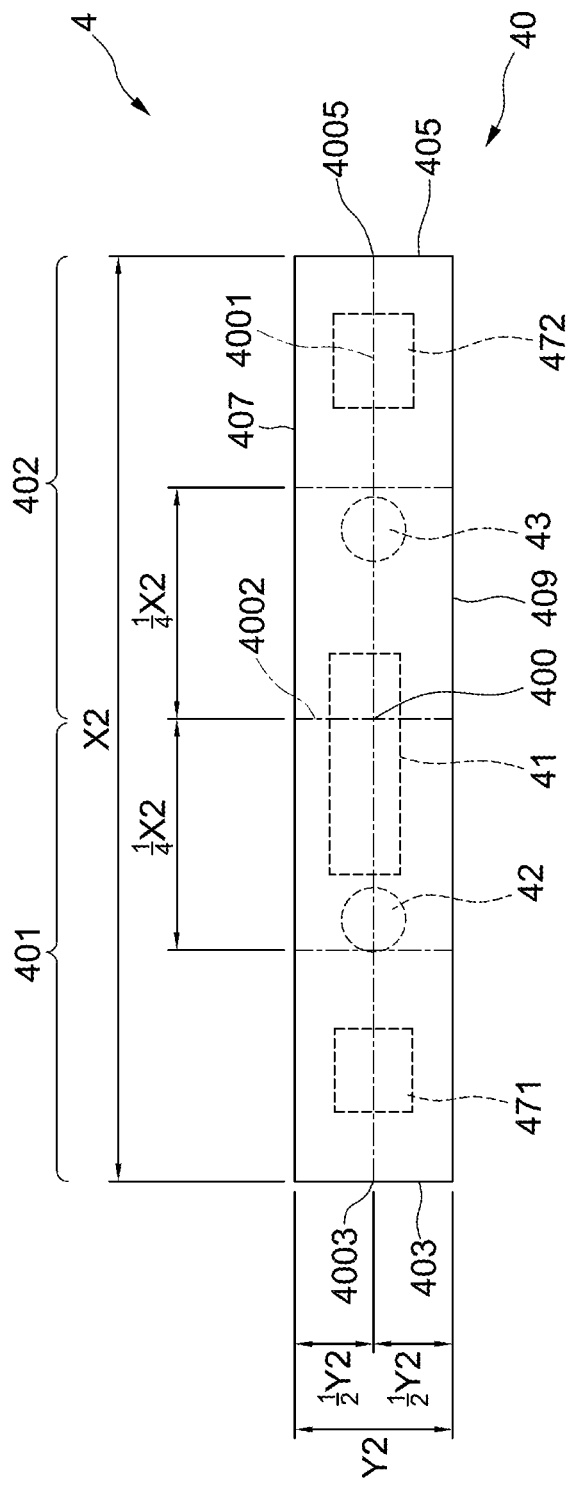
FIG. 4 is a schematic top view of an electronic device in accordance with some embodiments of the present disclosure.

FIG. 4 is a schematic top view of an electronic device 4 in accordance with some embodiments of the present disclosure. In some embodiments of the present disclosure, the electronic device 4 is the same as, or similar to, the electronic device 1 shown in FIG. 1A. In some embodiments of the present disclosure, the electronic device 4 is the same as, or similar to, the electronic device 2 shown in FIG. 2A. Referring to FIG. 4, the electronic device 4 has a flexible body 40. The flexible body 40 may have a geometric shape from a top view perspective. In some embodiments of the present disclosure, the flexible body 40 has a rectangular shape. The geometric shape of the flexible body 40 may define a geometric center 400, a major axis 4001 passing through the geometric center 400 and a minor axis 4002 passing through the geometric center 400 and perpendicular to the major axis 4001. The flexible body 400 of the electronic device 40 may have a first portion 401 and a second portion 402. In some embodiments of the present disclosure, the flexible body 400 is divided into the first portion 401 and the second portion 402 by the minor axis 4002. That is, the first portion 401 and the second portion 402 may be connected to each other and a junction of the first portion 401 and the second portion 402 may be located at the minor axis 4002. The electronic device 40 may have an electronic component 41 disposed in the first portion 401 and the second portion 402 of the flexible body 400. That is, the electronic component 41 may pass across the minor axis 4002.

As shown in FIG. 4, the electronic device 4 may have a magnetic element 42 disposed in the first portion 401 of the flexible body 40 and a magnetic element 43 disposed in the second portion 402 of the flexible body 40. In some embodiments of the present disclosure, the major axis 4001 may substantially pass through the magnetic element 42 and the magnetic element 43 from the top view perspective. In some embodiments of the present disclosure, a horizontal distance between the minor axis 4002 and the magnetic element 42 is substantially equal to a horizontal distance between the minor axis 4002 and the magnetic element 43. In some embodiments of the present disclosure, the horizontal distance between the minor axis 4002 and the magnetic element 42 is smaller than a horizontal distance between an end 4003 of the major axis 4001 and the magnetic element 42. In some embodiments of the present disclosure, the end 4003 is an intersection point of the major axis 4001 and a lateral side 403 of the flexible body 40. That is, a horizontal distance between the minor axis 4002 and the magnetic element 42 is smaller than a horizontal distance between the end 4003 and the magnetic element 42. Thus, a horizontal distance between the junction of the first portion 401 and 402 and the magnetic element 42 is smaller than a horizontal distance between the lateral side 403 of the flexible body 40 and the magnetic element 42. In some embodiments of the present disclosure, the horizontal distance between the minor axis 4002 and the magnetic element 43 is smaller than a horizontal distance between an end 4005 of the major axis 4001 and the magnetic element 43. In some embodiments of the present disclosure, the end 4005 is an intersection point of the major axis 4001 and a lateral side 405 of the flexible body 40. That is, a horizontal distance between the minor axis 4002 and the magnetic element 43 is smaller than a horizontal distance between the end 4005 and the magnetic element 43. Thus, a horizontal distance between the junction of the first portion 401 and 402 and the magnetic element 43 is smaller than a horizontal distance between the lateral side 405 of the flexible body 40 and the magnetic element 43. In some embodiments of the present disclosure, the horizontal distance between the end 4003 of the major axis 4001 and the magnetic element 42 is greater than ½ of the horizontal distance between the end 4003 of the major axis 4001 and the minor axis 4002. In some embodiments of the present disclosure, the horizontal distance between the end 4003 of the major axis 4001 and the magnetic element 42 is smaller than ¾ of a horizontal distance between the end 4003 of the major axis 4001 and the minor axis 4002 That is, the horizontal distance between the lateral side 403 of the flexible body 40 and the magnetic element 42 is smaller than ¾ of a horizontal distance between the lateral side 403 of the flexible body 40 and the junction of the first portion 401 and the second portion 402 and greater than ½ of the horizontal distance between the lateral side 403 of the flexible body 40 and the junction of the first portion 401 and the second portion 402. In some embodiments of the present disclosure, the horizontal distance between the end 4005 of the major axis 4001 and the magnetic element 43 is greater than ½ of the horizontal distance between the end 4005 of the major axis 4001 and the minor axis 4002. In some embodiments of the present disclosure, the horizontal distance between the end 4005 of the major axis 4001 and the magnetic element 43 is smaller than ¾ of a horizontal distance between the end 4005 of the major axis 4001 and the minor axis 4002. That is, the horizontal distance between the lateral side 405 of the flexible body 40 and the magnetic element 43 is smaller than ¾ of a horizontal distance between the end 405 of the flexible body 40 and the junction of the first portion 401 and the second portion 402 and greater than ½ of the horizontal distance between the lateral side 405 of the flexible body 40 and the junction of the first portion 401 and the second portion 402.

Referring to FIG. 4, a distance between the lateral side 403 and the lateral side 405 may be X2, and a distance between the lateral side 407 and the lateral side 409 may be Y1. A distance between the lateral side 403 and the magnetic element 42 may be greater than ¼ X2. A distance between the lateral side 403 and the magnetic element 42 may be smaller than ⅜ X2. A distance between the lateral side 405 and the magnetic element 43 may be greater than X2. A distance between the lateral side 405 and the magnetic element 43 may be smaller than ⅜ X2. Further, a distance between the lateral side 407 and the magnetic element 42 may be ½ Y2, and a distance between the lateral side 407 and the magnetic element 43 may be ½ Y2, and a distance between the lateral side 409 and the magnetic element 42 may be ½ Y2, and a distance between the lateral side 409 and the magnetic element 43 may be ½ Y2.

In addition, the electronic device 4 may include sensing elements 471 and 472. As shown in FIG. 4, the magnetic element 42 may not overlap the sensing element 471 from a top view perspective, and the magnetic element 43 may not overlap the sensing element 472 from the top view perspective.

Figure 5:
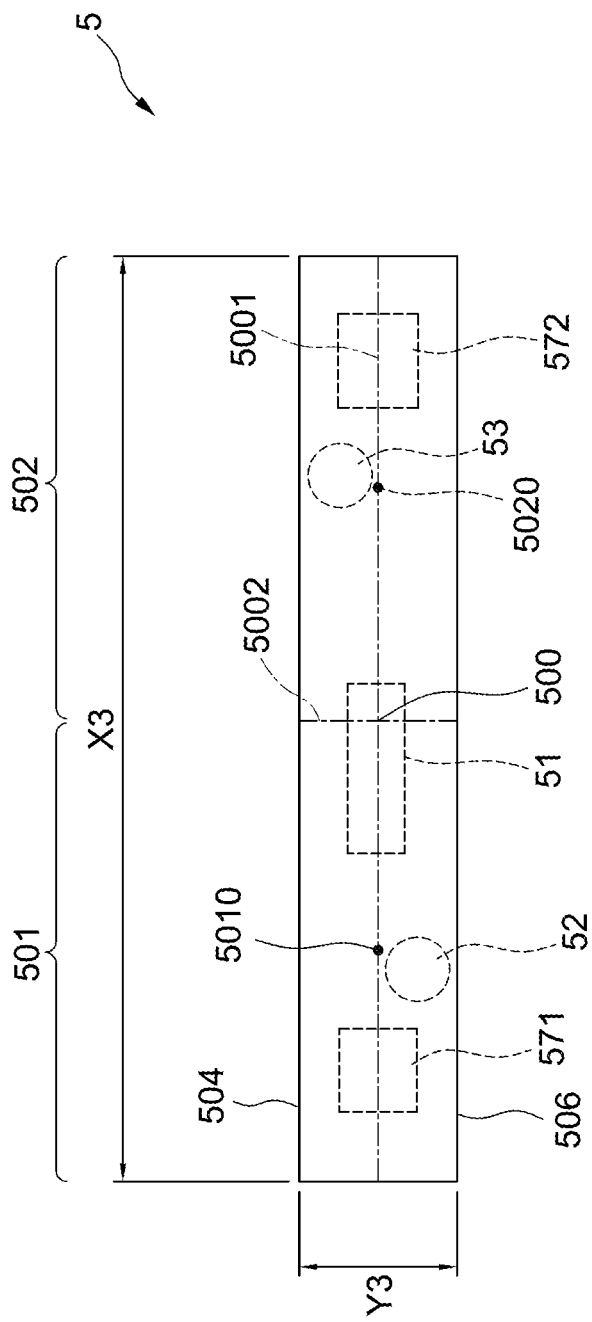
FIG. 5 is a schematic top view of an electronic device in accordance with some embodiments of the present disclosure.

FIG. 5 is a schematic top view of an electronic device 5 in accordance with some embodiments of the present disclosure. In some embodiments of the present disclosure, the electronic device 5 is the same as, or similar to, the electronic device 1 shown in FIG. 1A. In some embodiments of the present disclosure, the electronic device 5 is the same as, or similar to, the electronic device 2 shown in FIG. 2A. Referring to FIG. 5, the electronic device 5 has a flexible body 50. The flexible body 50 may have a geometric shape from a top view perspective. In some embodiments of the present disclosure, the flexible body 50 has a rectangular shape. The geometric shape of the flexible body 50 may define a geometric center 500, a major axis 5001 passing through the geometric center 500 and a minor axis 5002 passing through the geometric center 500 and perpendicular to the major axis 5001. The flexible body 500 of the electronic device 50 may have a first portion 501 and a second portion 502. In some embodiments of the present disclosure, the flexible body 500 is divided into the first portion 501 and the second portion 502 by the minor axis 5002. That is, the first portion 501 and the second portion 502 may be connected to each other and a junction of the first portion 501 and the second portion 502 may be located at the minor axis 5002. The electronic device 50 may have an electronic component 51 disposed in the first portion 501 and the second portion 502 of the flexible body 500. That is, the electronic component 51 may pass across the minor axis 5002.

As shown in FIG. 5, the electronic device 5 may have a magnetic element 52 disposed t in the first portion 501 of the flexible body 50 and a magnetic element 53 disposed in the second portion 502 of the flexible body 50. In some embodiments of the present disclosure, the major axis 5001 may not pass through the magnetic element 52 and the magnetic element 53 from the top view perspective. In some embodiments of the present disclosure, a horizontal distance between a side 504 of the flexible body 50 and the magnetic element 52 is greater than a horizontal distance between a side 506 of the flexible body 50 and the magnetic element 52. In some embodiments of the present disclosure, a horizontal distance between the side 506 of the flexible body 50 and the magnetic element 53 is greater than a horizontal distance between the side 504 of the flexible body 50 and the magnetic element 53. The magnetic elements 52 and 53 may be respectively positioned at two sides of the major axis 5001.

Referring to FIG. 5, the first portion 501 may have a geometric shape from a top view perspective. In some embodiments of the present disclosure, the first portion 501 has a rectangular shape. The geometric shape of the first portion 501 may define a geometric center 5010, and the magnetic element 52 is positioned to be offset from the geometric center 5010 of the first portion 501. In some embodiments of the present disclosure, the second portion 502 has a rectangular shape. The geometric shape of the second portion 502 may define a geometric center 5020, and the magnetic element 53 is positioned to be offset from the geometric center 5020 of the second portion 502. As shown in FIG. 5, a distance between the side 504 and 506 may be Y3. A distance between the magnetic element 52 and the side 504 may be greater than ½ Y3. A distance between the magnetic element 53 and the side 506 may be greater than ½ Y3. The major axis 5001 passing through the geometric center 5010 of the first portion 501 and the geometric center 5020 of the second portion 502, and the magnetic elements 52 and 53 are respectively arranged at two sides of the major axis 5001.

In addition, the electronic device 5 may include sensing elements 571 and 572. As shown in FIG. 5, the magnetic element 52 may not overlap the sensing element 571 from a top view perspective, and the magnetic element 53 may not overlap the sensing element 572 from the top view perspective.

Figure 6:
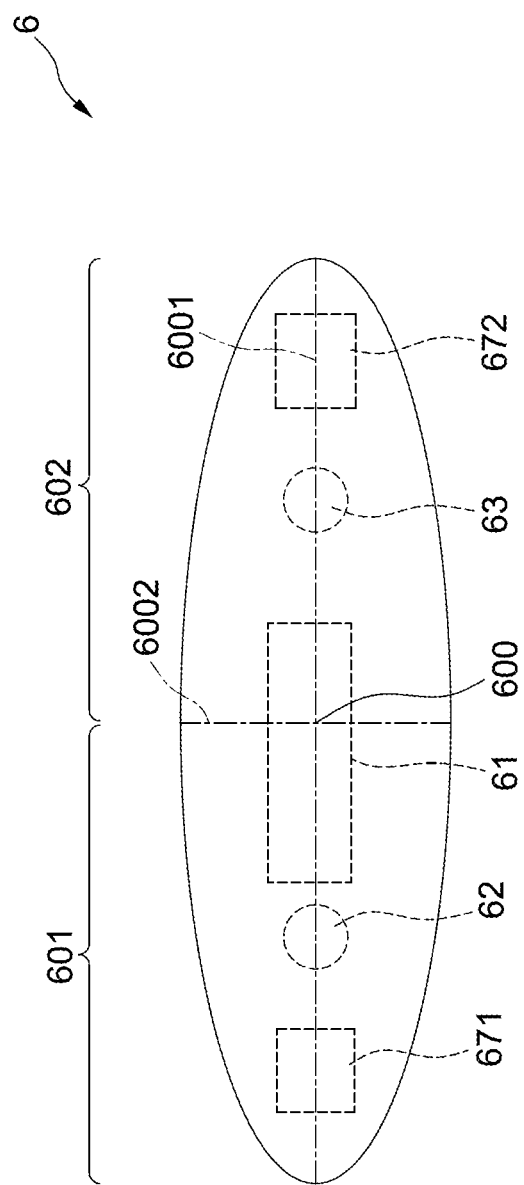
FIG. 6 is a schematic top view of an electronic device in accordance with some embodiments of the present disclosure.

FIG. 6 is a schematic top view of an electronic device 6 in accordance with some embodiments of the present disclosure. In some embodiments of the present disclosure, the electronic device 6 is the same as, or similar to, the electronic device 1 shown in FIG. 1A. In some embodiments of the present disclosure, the electronic device 6 is the same as, or similar to, the electronic device 2 shown in FIG. 2A. Referring to FIG. 6, the electronic device 6 has a flexible body 60. The flexible body 60 may have a geometric shape from a top view perspective. In some embodiments of the present disclosure, the flexible body 60 has a elliptical shape. The geometric shape of the flexible body 60 may define a geometric center 600, a major axis 6001 passing through the geometric center 600 and a minor axis 6002 passing through the geometric center 600 and perpendicular to the major axis 6001. The flexible body 600 of the electronic device 60 may have a first portion 601 and a second portion 602. In some embodiments of the present disclosure, the flexible body 600 is divided into the first portion 601 and the second portion 602 by the minor axis 6002. That is, the first portion 601 and the second portion 602 may be connected to each other and a junction of the first portion 601 and the second portion 602 may be located at the minor axis 6002. The electronic device 60 may have an electronic component 61 disposed in the first portion 601 and the second portion 602 of the flexible body 600. That is, the electronic component 61 may pass across the minor axis 6002.

As shown in FIG. 6, the electronic device 6 may have a magnetic element 62 disposed in the first portion 601 of the flexible body 60 and a magnetic element 63 disposed in the second portion 602 of the flexible body 60.

In addition, the electronic device 6 may include sensing elements 671 and 672. As shown in FIG. 6, the magnetic element 62 may not overlap the sensing element 671 from a top view perspective, and the magnetic element 63 may not overlap the sensing element 672 from the top view perspective.

As used herein, the singular terms "a," "an," and "the" may include a plurality of referents unless the context clearly dictates otherwise.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if the difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" parallel can refer to a range of angular variation relative to 0° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, "substantially" perpendicular can refer to a range of angular variation relative to 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range were explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein are described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations on the present disclosure.

What is claimed is:

1. An electronic device, comprising:
   a bendable body having a first portion and a second portion; and
   an electronic component located at the first portion and the second portion of the bendable body;
   wherein the first portion and the second portion are configured to repel each other within in a distance; and
   wherein the bendable body comprises a base supporting the electronic component and an encapsulant covering the electronic component, and wherein a first magnetic element and a second magnetic element is disposed in the base or the encapsulant.

2. The electronic device of claim 1, wherein the bendable body has a geometric shape from a top view perspective, and wherein the geometric shape of the bendable body defines a first axis passing through a geometric center of the geometric shape, and wherein the first axis passes through the first magnetic element located at the first portion of the bendable body and the second magnetic element located at the second portion of the bendable body from the top view perspective.

3. The electronic device of claim 2, wherein the geometric shape of the bendable body defines a second axis passing through the geometric center of the geometric shape and perpendicular to the first axis, and a horizontal distance between the first magnetic element and the second axis is substantially equal to a horizontal distance between the second magnetic element and the second axis.

4. The electronic device of claim 3, wherein the first axis has a first end closer to the first magnetic element than to the second magnetic element and a second end opposite to the first end, and wherein a horizontal distance between the first end of the first axis and the first magnetic element is substantially equal to or greater than the horizontal distance between first magnetic element and the second axis, and wherein a horizontal distance between the second end of the first axis and the second magnetic element is substantially equal to or greater than the horizontal distance between second magnetic element and the second axis.

5. The electronic device of claim 1, wherein the encapsulant has an upper surface, and wherein the first magnetic element has a first end portion and a second end portion, which is opposite to the first end portion of the first magnetic element and closer to the upper surface of the encapsulant than the first end portion of the first magnetic element, and wherein the second magnetic element has a first end portion and a second end portion, which is opposite to the first end portion of the second magnetic element and closer to the upper surface of the encapsulant than the first end portion of the second magnetic element, and wherein a magnetic polarity of the second end portion of the first magnetic element and a magnetic polarity of the second end portion of the second magnetic element are the same.

6. The electronic device of claim 1, wherein the first magnetic element is free from overlapping a sensing element of the electronic device from a top view perspective.

7. The electronic device of claim 1, wherein the first magnetic element overlaps an interconnection structure of the base from a top view perspective.

8. The electronic device of claim 1, wherein the first magnetic element is located at the first portion of the bendable body and the second magnetic element is located at the second portion of the bendable body, and wherein the first portion has a geometric shape from a top view perspective and the second portion has a geometric shape from a top view perspective, and wherein the first magnetic element is offset from a geometric center of the geometric shape of the first portion from the top view perspective and the second magnetic element is offset from a geometric center of the geometric shape of the second portion from the top view perspective.

9. The electronic device of claim 8, wherein the bendable body defines a third axis passing through the geometric center of the geometric shape of the first portion and the geometric center of the geometric shape of the second portion, and wherein the first magnetic element and second magnetic element are at different sides of the third axis.

10. An electronic device, comprising:
a main body having a first portion and a second portion;
an electronic component disposed in the main body; and
a magnetic assembly comprising a first magnetic element in the first portion of the main body and a second magnetic element in the second portion of the main body;
wherein the magnetic assembly is configured to resist excessive relative movement between the first portion and the second portion of the main body;
wherein the main body has a geometric shape from a top view perspective, and wherein the geometric shape of the main body has an axis passing through a geometric center of the geometric shape of the main body, and wherein the axis extends between the first magnetic element and the second magnetic element.

11. The electronic device of claim 10, wherein the electronic component is arranged between the first magnetic element and the second magnetic element.

12. The electronic device of claim 11, wherein the first magnetic element and the second magnetic element are configured to repel each other when the main body is bent and the first portion and the second portion of the main body are moved toward each other.

13. An electronic device, comprising:
a bendable body having a first end and a second end opposite to the first end and defining a first central axis between the first end and the second end;
an electronic component disposed in the bendable body,
a first magnetic element disposed in the bendable body and closer to the first central axis than the first end; and
a second magnetic element disposed in the bendable body and closer to the first central axis than the second end.

14. The electronic device of claim 13, further comprising a first sensing element and a second sensing element, and wherein the first magnetic element is disposed between the electronic component and the first sensing element from a top view perspective, and wherein the second magnetic element is disposed between the electronic component and the second sensing element from the top view perspective.

15. The electronic device of claim 14, wherein the bendable body comprises a base supporting the electronic component and an encapsulant covering the electronic component, and wherein a portion of the first sensing element and a portion of the second sensing element are underneath a lower surface of the base 108 and configured to detect a biosignal signal of a user.

16. The electronic device of claim 15, wherein the base comprises an interconnection structure, and wherein the interconnection structure partially overlaps the first magnetic element or the second magnetic element from a top view perspective, and wherein the first sensing element or the second sensing element is electrically connected to the electronic component through the interconnection structure.

17. The electronic device of claim 13, wherein the first magnetic element and the second magnetic element are configured to position the electronic device over a charger.

18. The electronic device of claim 17, wherein the bendable body comprises a base supporting the electronic component and an encapsulant covering the electronic component, and wherein the first magnetic element and the second magnetic element are at least partially disposed within the base.

* * * * *